United States Patent
Parks

(10) Patent No.: US 6,733,779 B2
(45) Date of Patent: May 11, 2004

(54) METHOD OF TREATING BENIGN PROSTATIC HYPERPLASIA AND OTHER BENIGN PROSTATE CONDITIONS

(76) Inventor: L. Dean Parks, 2420 SE. 15th St., Ocala, FL (US) 34471

( * ) Notice: Subject to any disclaimer, the term of this patent is extended or adjusted under 35 U.S.C. 154(b) by 0 days.

(21) Appl. No.: 09/953,620

(22) Filed: Sep. 17, 2001

(65) Prior Publication Data

US 2002/0077359 A1 Jun. 20, 2002

Related U.S. Application Data

(63) Continuation-in-part of application No. 09/383,608, filed on Aug. 26, 1999, now abandoned.

(51) Int. Cl.$^7$ .............................. A61K 9/48; A61K 9/20; A61K 9/14; A61K 9/16
(52) U.S. Cl. ....................... 424/451; 424/452; 424/464; 424/465; 424/489; 424/490; 424/491
(58) Field of Search ................................. 424/451, 452, 424/464, 465, 489, 490, 491; 514/324, 376

(56) References Cited

U.S. PATENT DOCUMENTS

| | | | | |
|---|---|---|---|---|
| 5,612,354 A | * | 3/1997 | Sanz et al. | 514/314 |
| 5,821,254 A | * | 10/1998 | Sporn et al. | 514/324 |
| 5,843,994 A | * | 12/1998 | Samid | 514/510 |
| 6,043,277 A | * | 3/2000 | Rephaeli et al. | 514/548 |
| 6,087,385 A | * | 7/2000 | Pershadsingh et al. | 514/376 |
| 6,306,426 B1 | * | 10/2001 | Olejnik et al. | 424/426 |
| 6,399,115 B2 | * | 6/2002 | Revel | 424/727 |
| 6,413,535 B1 | * | 7/2002 | Steiner et al. | 424/422 |

OTHER PUBLICATIONS

Daiya et al., Inhibition of Tumorigenic Potential and Prostate–Specific Antigen Expression in LNCAP Human Prostate Cancer Cell Line by 13–cis–retinoic acid; Inter. J. Cancer: 59, 126–132 (1994).*

Stearns et al., "Liarozole and 13–cis–retinoic acid anti–prostatic tumor activity"; Cancer Res 1993 Jul 1; 53(3):3073–7.*

Pili et al., "Combination of phenylbutyrate and 13–cis–retinoic acid inhibits prostate tumor growth and angiogenesis"; Cancer Re Feb. 15, 2001; 61(4): 1477–85.*

Dahiya, et al., International Journal of Cancer, 1894, Oct. 1, 59(1) : 126 132, entitled "Inhibition of Tumorgenic Potential and Prostage–Specific Antigen in Human Prostate Cancer Cell Lines by 13–Cis Retinoic Acid."

* cited by examiner

Primary Examiner—Thurman K. Page
Assistant Examiner—S. Tran
(74) Attorney, Agent, or Firm—M. K. Silverman; Yi Li

(57) ABSTRACT

Methods of treatment of benign prostatic hyperplasia and reduction of the level of the prostate specific antigen (PSA) of benign prostate conditions are disclosed. The treatment method includes an initial treatment of patients with orally administration of an initial dosage of about 40 mg 13 cis-retinoic acid daily for a period from about ten days to about twenty days, and followed by a sustaining treatment of the patients with orally administration of a sustaining dosage of about 40 mg 13 cis-retinoic acid about every five to seven days in a sustaining period.

8 Claims, No Drawings

METHOD OF TREATING BENIGN PROSTATIC HYPERPLASIA AND OTHER BENIGN PROSTATE CONDITIONS

CROSS REFERENCE TO RELATED APPLICATION

This application is a continuation-in-part of patent application Ser. No. 09/383,608 filed Aug. 26, 1999, which is now abandoned herein incorporated by reference in its entirety.

FIELD OF THE INVENTION

The present invention relates to methods for treating benign prostate hyperplasia and reducing the level of prostate specific antigen of benign prostate conditions. More specifically, the methods utilize 13 cis-retinoic acid to effectively treat benign prostate hyperplasia, and to reduce the level of prostate specific antigen of the patients with benign prostate conditions.

BACKGROUND OF THE INVENTION

The three most common prostate health problems facing men and their families today are benign prostatic hyperplasia (BPH), prostate cancer, and prostatitis. Each of these conditions affects the prostate differently. Benign prostate hyperplasia is the most common benign neoplasm (non cancerous enlargement of the prostate gland) in men, and has a high prevalence that increases with age. The increase in size of the prostate inside its capsule exerts pressure on the urethra, which passes through the capsule, resulting in obstruction to urine flow. Half of all men have BPH identifiable histologically at age 60 years, and by 85 years the prevalence is about 90%. In the United States about 25% of men will be treated for BPH by age 80, and over 300,000 surgical procedures are performed each year for BPH (mostly transurethral resection of the prostate, TURP). This makes TURP the second most common surgical procedure, second only to cataract surgery—at a cost estimated at $2 billion per year. Experts do not yet know what causes BPH, but the condition may be related to the hormone testosterone and its relationship to other hormones that change during the aging process.

There are a number of treatment options for BPH. These include watchful waiting, medical therapy such as alpha blocker therapy and finasteride therapy, balloon dilatation and various surgical procedures such as transurethral incision of the prostate (TUIP), transurethral resection of the prostate (TURP), and open prostatectomy. Few treatments are without any adverse consequences, and this is particularly so with treatments with BPH, where there is a delicate balancing act between the benefits and demerits of the treatments available. The adverse events following treatment for BPH include impotence (for various surgical procedures ranging from about 4% to 40%, the incidence of impotence is also increased after some medical treatments), incontinence (stress incontinence about 3% after surgery, with total urinary incontinence approaching 1%), and the need for re-treatment. Combined analysis of published data estimated that the mean probability for perioperative mortality (death within 90 days of a procedure) was 1.5% for TURP. For open surgery it was 2.4% and for balloon dilation it was 3.5%.

It is well known that prostate specific antigen (PSA), a protein produced by prostate cells, is frequently present at elevated levels in the blood of men who have prostate cancer. The U.S. Food and Drug Administration has approved a PSA test for use in conjunction with a digital rectal exam to help detect prostate cancer in men age 50 or older and for monitoring prostate cancer patients after treatment. However, much remains unknown about the interpretation of PSA levels, the test's ability to discriminate cancer from benign prostate conditions, and the best course of action following a finding of elevated PSA. Furthermore, clinically it is known that BPH and prostatitis can cause elevated PSA.

13-cis retinoic acid, more generally known as retinoic acid, also referred to as isotretinoin, and sold under the Roche trademark Accutane, has long been known as a topical and oral dermatologic agent used in the treatment of acne vulgrais and several other skin diseases. 13-cis retinoic acid inhibits sebaceous gland function and keratinization. The exact mechanism of action of Accutane in treating acne is unknown. Since retinoic acid is a teratogneic drug and, because of the mutagenic effects associated with such drugs, it has only gradually entered the mainstream of medicine.

Experimentation in non-dermatologic applications of retinoic acid appeared in the literature in 1992 in an investigation at the University of California School of Medicine (Department of Urology), in San Francisco, this with reference to the effect of 13-cis-retinoic acid upon human prostate cancer cells. Since 1992, the research group at the University of California, headed by Dr. Dahiya, established the effect of retinoic acid in the downregulation of saturated fatty acids coupled with the upregulation of unsaturated fatty acids in human prostate cancer cells. As such, saturated fatty acids, which are believed to play a significant role in prostate cancer, were inhibited while unsaturated fatty acids, which are believed to act in a protective way relative to such cancers, were increased in cell lines.

However, isotretinoin or retinoic acid has not been used for treating benign prostate hyperplasia, or for reducing the level of prostate specific antigen of benign prostate conditions.

SUMMARY OF THE INVENTION

In one embodiment, the present invention relates to a method of treating benign prostatic hyperplasia. The method comprises the steps of (a) orally administering about 40 mg of 13-cis-retinoic acid daily for an initial treatment period from about ten days to about twenty days; and (b) thereafter orally administering about 40 mg of 13-cis-retinoic acid in about every five to seven days in a sustaining period.

In a further embodiment, the present invention relates to a method of reducing the level of prostate specific antigen (PSA) of patients. The method comprises the steps of (a) orally administering about 40 mg of 13-cis-retinoic acid daily for an initial treatment period from about ten days to about twenty days; and (b) thereafter orally administering about 40 mg of 13-cis-retinoic acid in about every five to seven days in a sustaining period.

It is accordingly an object of the present invention to provide a method of treating benign prostatic hyperplasia and related symptoms such as reduced or constricted urine stream and urinary retention.

It is another object to provide a method of reduction of the level of the prostate specific antigen of benign prostate conditions.

The above and yet other objects and advantages of the present invention will become apparent from the hereinafter set forth Detailed Description of the Invention and Claims appended herewith.

DETAILED DESCRIPTION OF THE INVENTION

The instant invention derived from the observation that the human prostate comprises a modified sebaceous gland and that, given the many years of usage of successful Accutane/isotretinoic/retinoic acid in the treatment of acne, this through the shrinking of sebaceous glands within the face and neck, that a similar action might occur upon the prostate gland if Accutane were taken as an oral medication.

Operating with the informed consent of approximately twelve patients exhibiting either or both an elevated PSA, that is, patients with a PSA of greater than 4 ng/ml and/or with exhibiting benign prostatic hyperplasia, the patients were treated with Accutane manufactured by Roche.

The treatment method involves essentially two periods: an initial treatment, and a sustaining treatment. First, in the initial treatment the patients orally administrate an initial dosage about 40 mg of 13-cis-retinoic acid daily for a period from about ten days to about twenty days. Thereafter, the patients orally administrate a sustaining dosage about 40 mg of 13-cis-retinoic acid about every five to seven days in a sustaining period. Typically, the sustaining period is about one year. However, it can be extended longer if extended maintenance is needed. Preferably, the initial treatment period is about fourteen days, because beyond fourteen days side effects of the medicine, such as tenderness at sites of old injuries to the fibro-musculo-skeletal system, dry skin, chapped lips, dry eyes, and dry nose, tend to occur. If these side effects occur during the initial treatment period, they normally subside after the sustaining dosage is instituted.

In the initial treatment, 40 mg of 13-cis-retinoic acid can be administrated in a single dose, or divided doses. Commercially, Accutane has three available doses, 10 mg, 20 mg, and 40 mg soft gelatin capsules. The patients can either take one 40 mg capsule, or take two 20 mg capsules daily. The same applies to the dosage in the sustaining treatment. For convenience, the patients can take one 40 mg dose every five to seven days.

The initial dosage of about 40 mg 13-cis-retinoic acid daily is determined based on average men's body weight of about 160 lbs, i.e. at about 0.25 mg/lb of body weight. For patients who weigh substantially above or less than the average body weight, the dosage described above can be adjusted accordingly. The same principle applies to the sustaining dosage.

The 13-cis-retinoic acid used for the purpose of the present invention can be in various forms, such as powders, pills, capsules, tablets, and liquids. The liquids comprise 13-cis-retinoic acid in a suitable pharmaceutical media, such as water, glycols, oils, alcohols, and syrups.

This treatment method resulted in subjective as well as objective amelioration of benign prostatic hyperplasia and symptoms thereof, and a measurable reduction in the prostate specific antigen (PSA). In particular, through examination of these patients and through their own anecdotal comments, a reduction in prostate enlargement was confirmed. Furthermore, the blood test results showed that PSA levels had been dramatically reduced to levels in a range of b 0to 2 ng/ml among these patients.

Example 1 to 4 illustrate clinical effectiveness of the above described treatment method. It was found that none of the conditions of these patients worsened either in terms of PSA or hyperplasia, and none progressed into any form of diagnosable malignancy. Further, no serious adverse side effects or contra-indications of any kind were observed among the patients in the informal trials.

EXAMPLE 1

A patient started a slowly progressive prostatic enlargement and attenuated urine stream 20 years ago. Hand examination confirmed a palpably enlarged prostate, probably secondary to post vasectomy prostatitis.

The patient was placed on Accutane 40 mg orally for 14 days in the initial treatment. Then he was placed on sustaining dose of 40 mg every 5 days for about one year.

The patient's symptoms improved steadily. His prostate decreased in palpable size, and PSA dropped from 4 to less than one.

No adverse side effects were noted other than drying of lips and some musculo-skeletal soreness at sites of old injuries to the fingers and neck. This soreness subsided slowly after the sustaining dose was instituted. Blood chemistries remained normal on this low sustaining dosage.

EXAMPLE 2

The patient had prior histories of urethritis and prostatitis from sexually transmitted diseases. The patient had steadily increasing prostatic enlargement, with decreasing urine flow, plus urgency and nocturia. PSA was 3, and prostate palpably enlarged.

The patient was placed on Accutane 40 mg orally for 14 days. Then the dosage was decreased to 40 mg every 5 days for about one year.

The patient had steady improvement in symptoms and after 6 months PSA had dropped to less than one. No adverse side effects were observed from administration of the Accutane.

EXAMPLE 3

A patient had history of posttraumatic prostatitis caused by a bicycle accident in 1987. The patient's condition became chronic especially after long auto trips, and required frequent courses of antibiotics and steroids to calm the inflammation. PSA was 5.

The patient was placed on Accutane 40 mg daily for 14 days. Thereafter, the patient had a maintenance dosage of 40 mg every 5 days for about one year.

The patient rapidly became symptom free after the initial treatment, and had remained so during the sustaining period. PSA dropped to less than 1.

EXAMPLE 4

The patient had a history of sexually transmitted diseases in college and subsequent history of prostatitis. Enlargement of prostate was noted 6 years prior to the Accutane treatment, with steadily worsening urinary tenesmus.

The patient was placed on Accutane 40 mg per day. After 14 days, the dosage was decreased to 40 mg every 5 days for about one year.

The patient's symptoms readily improved and PSA dropped from 4 to less than 1 within 6 months.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

What is claimed is:

1. A method of treatment of benign prostatic hyperplasia consisting essentially of the steps of:

(a) orally administering to a patient of an initial dosage of about 40 mg of 13-cis-retinoic acid daily for an initial treatment period from about ten days to about twenty days, wherein said 13-cis-retinoic acid is in a form selected from the group consisting of powder, pill, capsule, tablet, ant liquid, and (b) thereafter orally administering a sustaining dosage of about 40 mg of 13-cis-retinoic acid about every five to seven days in a sustaining period.

2. The method of claim 1 wherein said sustaining period is about one year.

3. The method of claim 1 wherein said initial treatment period is about fourteen days.

4. The method of claim 1 wherein said liquids comprise 13-cis-retinoic acid in a pharmaceutical media selected from the group consisting of water, glycol, oil, alcohol, and syrup.

5. A method of reduction of a level of a prostate specific antigen (PSA) of benign prostate conditions consisting essentially of the steps of:

(a) orally administering to a patient of an initial dosage of about 40 mg of 13-cis-retinoic acid daily for an initial treatment period from about ten days to about twenty days, wherein said 13-cis-retinoic acid is in a form selected from the group consisting of powder, pill, capsule, tablet, ant liquid, and (b) thereafter orally administering a sustaining dosage of about 40 mg of 13-cis-retinoic acid about every five to seven days in a sustaining period.

6. The method of claim 5 wherein said sustaining period is about one year.

7. The method of claim 5 wherein said initial treatment period is about fourteen days.

8. The method of claim 6 wherein said liquids comprise 13-cis-retinoic acid in a pharmaceutical media selected from the group consisting of water, glycol, oil, alcohol, and syrup.

* * * * *